United States Patent [19]

Brezinski

[11] 4,097,735
[45] Jun. 27, 1978

[54] TESTING THE OPERATION OF A RECORDING FLUOROMETER/DENSITOMETER

[75] Inventor: Donald P. Brezinski, Corning, N.Y.

[73] Assignee: Corning Glass Works, Corning, N.Y.

[21] Appl. No.: 799,943

[22] Filed: May 24, 1977

[51] Int. Cl.² ................... G01D 18/00; G01N 21/38
[52] U.S. Cl. ................................ 250/252; 250/461 R
[58] Field of Search ........... 250/252, 458, 459, 461 R, 250/461 B; 235/151.35

[56] References Cited

U.S. PATENT DOCUMENTS 3,706,877   12/1972   Clifford, Jr. et al. ............ 235/151.35

*Primary Examiner*—Davis L. Willis
*Attorney, Agent, or Firm*—Richard E. Kurtz; Walter S. Zebrowski; Clarence R. Patty, Jr.

[57] ABSTRACT

A test sample for testing a recording fluorometer/densitometer has multiple tracks with features that generate detector outputs indicating performance parameters. In the normal mode of operation the instrument scans the optical absorbance or fluorescence characteristics of electrophoretic samples in a plurality of tracks on a thin agarose film plate. In order to correctly record the optical characteristics of these electrophoretic samples, the instrument must respond linearly and with the correct range, resolution and alignment. A test sample is scanned in the same manner as a normal sample. The resulting instrument output provides easily analyzed information on fluorometric and densitometric performance parameters including linearity, range, spatial resolution, slit and scan path alignments, scan speed and excitation uniformities, response time, noise, electrical and optical offsets, integration accuracies, automatic gain and zeroing accuracies.

12 Claims, 5 Drawing Figures

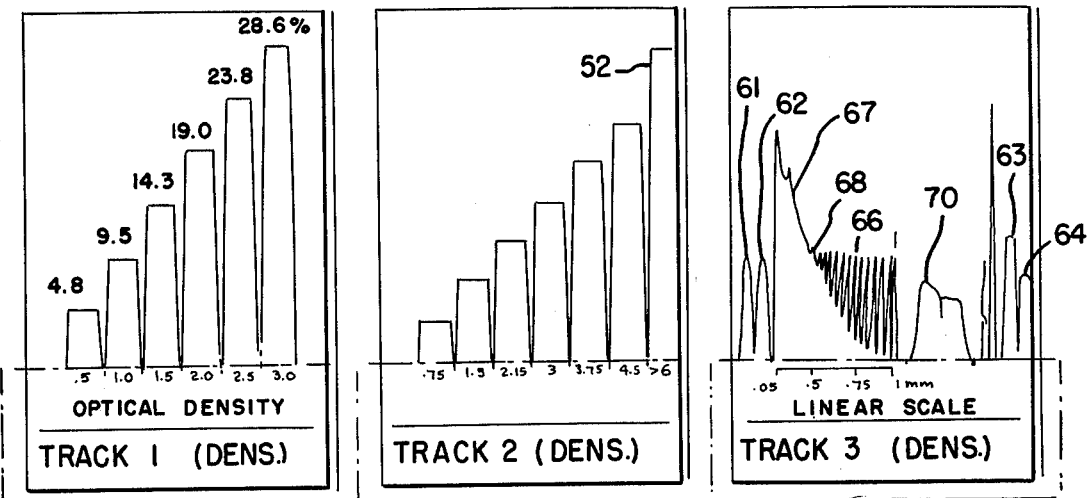
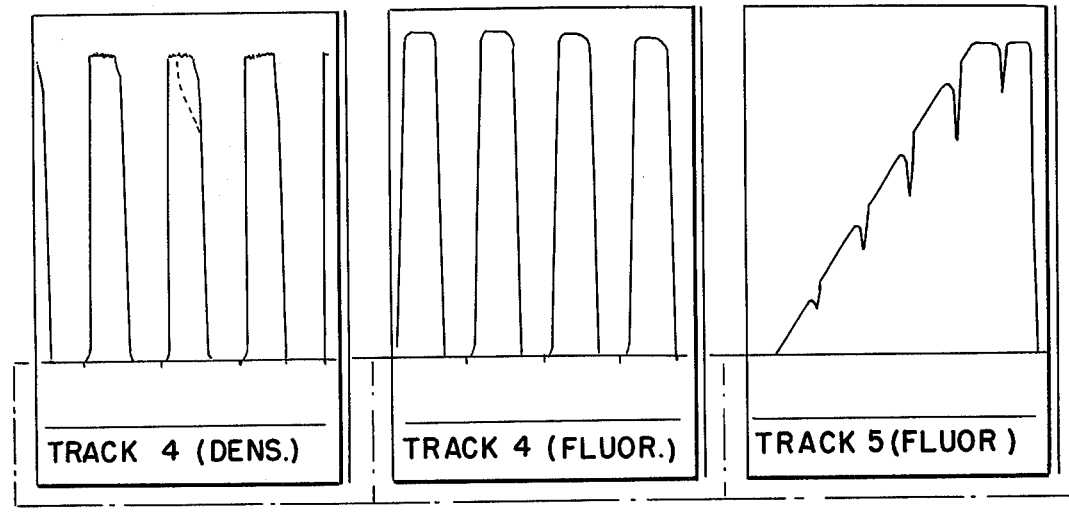
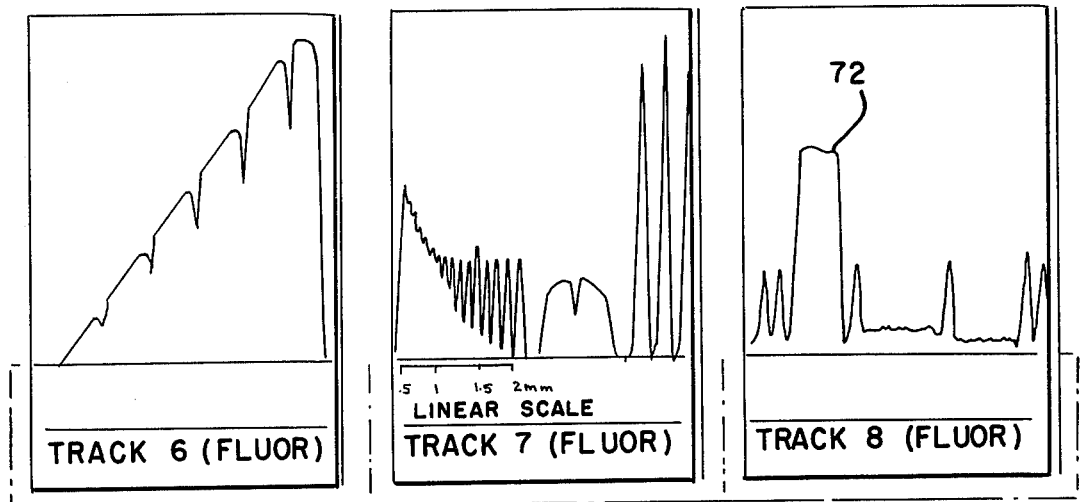
Fig. 5

TESTING THE OPERATION OF A RECORDING FLUOROMETER/DENSITOMETER

BACKGROUND OF THE INVENTION

This invention relates to recording fluorometer/densitometers and more particularly to methods of testing them.

A recording fluorometer/densitometer is used to analyze the electrophoretic characteristics of a clinical sample.

U.S. Pat. Nos. 3,479,265 and 3,635,808 disclose thin film agarose sample plates which can be used as the electrophoretic medium. The thin film samples of these patents are particularly convenient for handling and storage.

These samples are analyzed by fluorometric or densitometric optical detection. One instrument for automatically making analyses of this type is described in U.S. Pat. No. 3,706,877. In such an instrument, the area under selected peaks of the curve is determined by integration.

RELATED APPLICATIONS

Copending applications Ser. No. 800,004, filed May 24, 1977, Ser. No. 800,005, filed May 24, 1977, Ser. No. 799,942, May 24, 1977, and Ser. No. 799,944, filed May 24, 1977, describe an instrument in which an electrophoretic sample is scanned with fluorometric or densitometric light.

It is desired to provide a reliable, fast, easy to perform method of testing the operating parameters of such instruments.

SUMMARY OF THE INVENTION

In accordance with this invention a test sample having a plurality of tracks bearing optical density and/or fluorescent features is scanned for the purpose of evaluating instrument performance.

In accordance with the invention a test sample includes multiple tracks which bear features that generate recorder outputs indicating linearity, range, resolution and alignment of the instrument.

The multiple track test sample of this invention eliminates elaborate electrical, mechanical or chemical procedures previously required for routine instrument testing.

The foregoing and other objects, features and advantages of the invention will be understood from the following more detailed description and appended claims.

DESCRIPTION OF THE DRAWINGS

FIG. 5 shows the recorded response to the test sample.

DESCRIPTION OF THE PREFERRED EMBODIMENT

Figure 1:
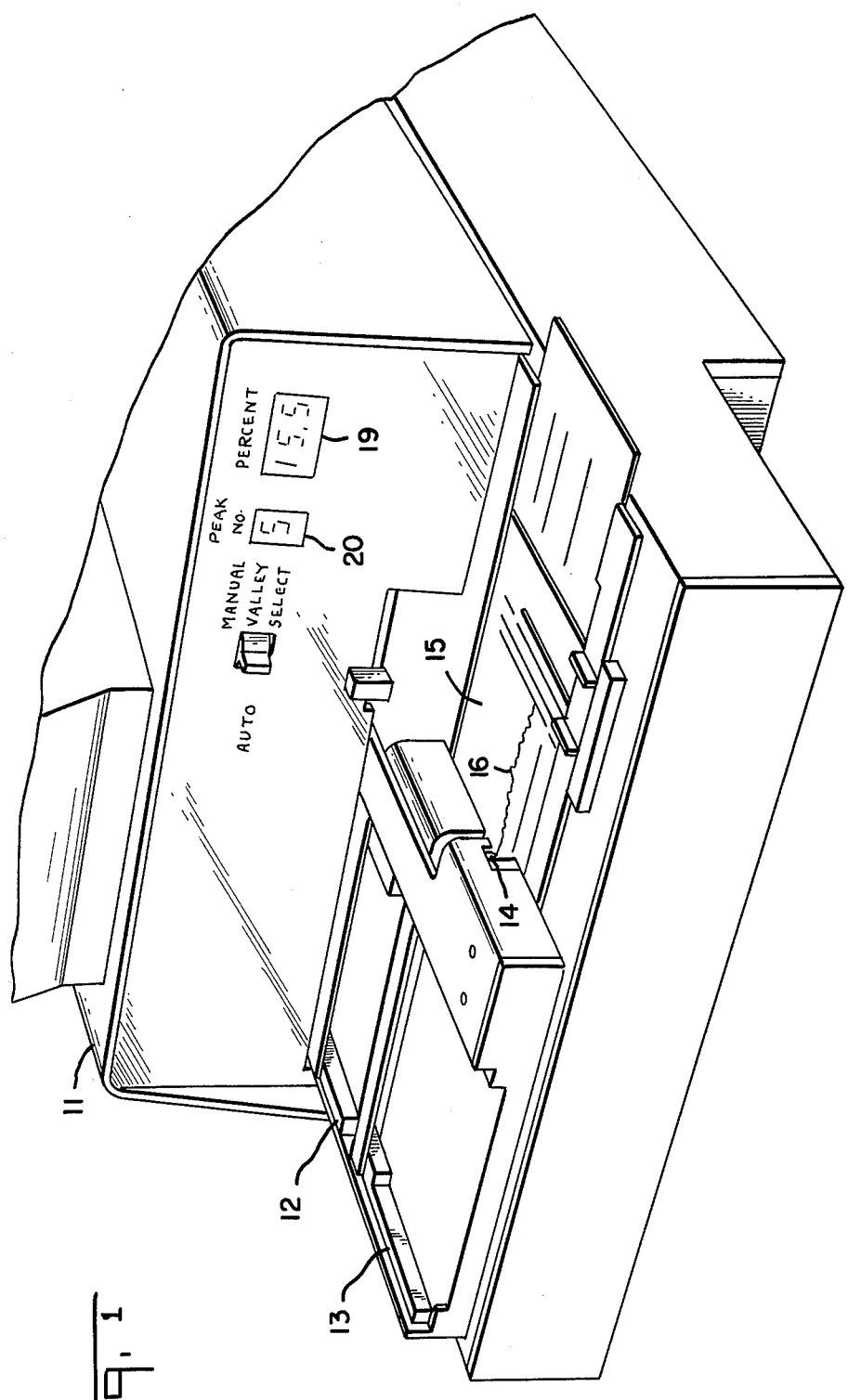
FIG. 1 shows the electrophoretic sample analyzer of this invention.

The instrument includes a case 11 which encloses fluorometric and densitometric sources of analysis energy and optics. For automatic recording, the film sample is inserted in the sample holder 12. The sample holder slides into the case between the light sources and the detection optics. The sample stage 13 moves in a horizontal direction to scan the analysis energy and optics across the film. Concurrently, a recording pen 14 moves across the chart 15. The pen 14 is moved along chart 15 by the same movement which scans the sample across the source. A detector measures analysis energy intensity from the sample, and the recording system responds to the output of the detector to move the recording pen 14 othogonally to the scanning motion. This produces a record 16 of optical density or fluorescence across the sample.

A record is produced by a forward, left to right, scan and a return, right to left, scan. On the forward scan, automatic circuits are conditioned to store the maximum and minimum of the detected analysis energy. These values are used to automatically set the scale and base line for the record. On the return scan, the record 16 is drawn on the chart 15 and valleys between peaks are automatically selected. An integrator integrates the area of each peak under the record 16. The area of each peak as the percentage of the total area under the record 16 is determined. These percentages are displayed on digital display 19. Digital display 20 displays the number of the peak.

Figure 2:
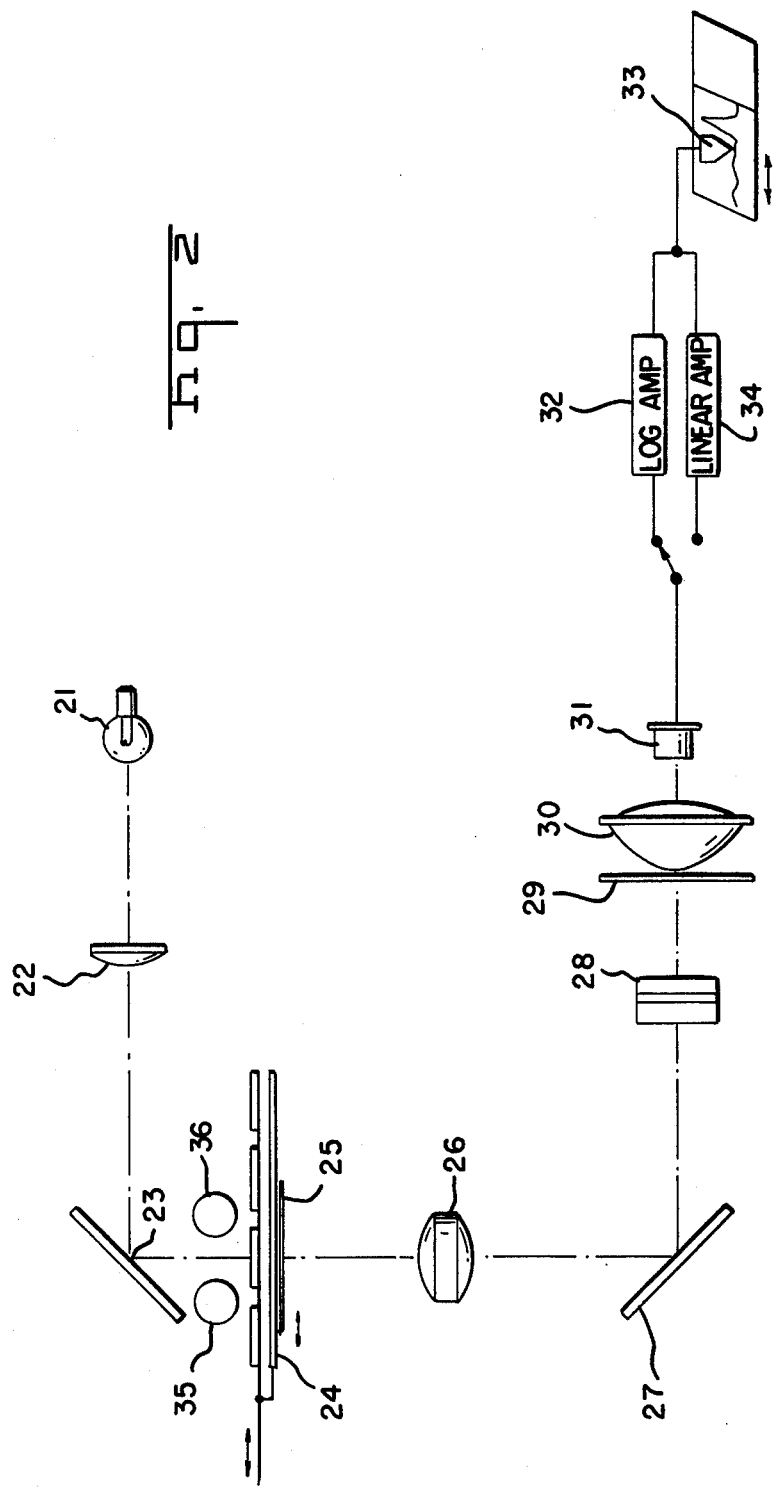
FIG. 2 shows the optical system of such an instrument.

Referring to FIG. 2, the instrument includes an incandescent lamp 21 used as a source for making densitometric measurements at different visible wavelengths. Lens 22 and fold mirror 23 direct light through one of the three densitometric filters mounted on the filter holder 24 which is moved to place the appropriate filter in the optical axis. An aperture is in close proximity to the sample 25 and determines the optical resolution in densitometry. Hereafter, the effective area of the detector exposed to light from the sample is referred to as the slit.

The sample is moved from right to left during its scanning and it absorbs light in accordance with the optical density of the sample. Light passing through the sample is gathered by the objective lens 26, reflected by the mirror 27 and passes through secondary filter 28. Densitometric light passing through is imaged within the second aperture 29 so all of the densitometry light passes through this second aperture.

An aspheric lens 30 forms an image of the objective lens exit pupil on the photo diode detector 31. The output of detector 31 is applied to a logarithmic amplifier 32 which produces an electrical signal proportional to optical density or absorbance of the sample. This signal is applied to the recording device 33 which records absorbance.

In order to use the same detector 31 and recording device 33 for both densitometric and fluorometric measurements, it is necessary to use logarithmic amplifier 32 in densitometric measurements and linear amplifier 34 in fluorometric measurements.

In the fluorometric mode of operation, light from ultraviolet lamps 35 and 36 passes through an ultraviolet transmission filter to excite the sample. The emitted fluorescence is sensed by the detector 31.

Figure 3:
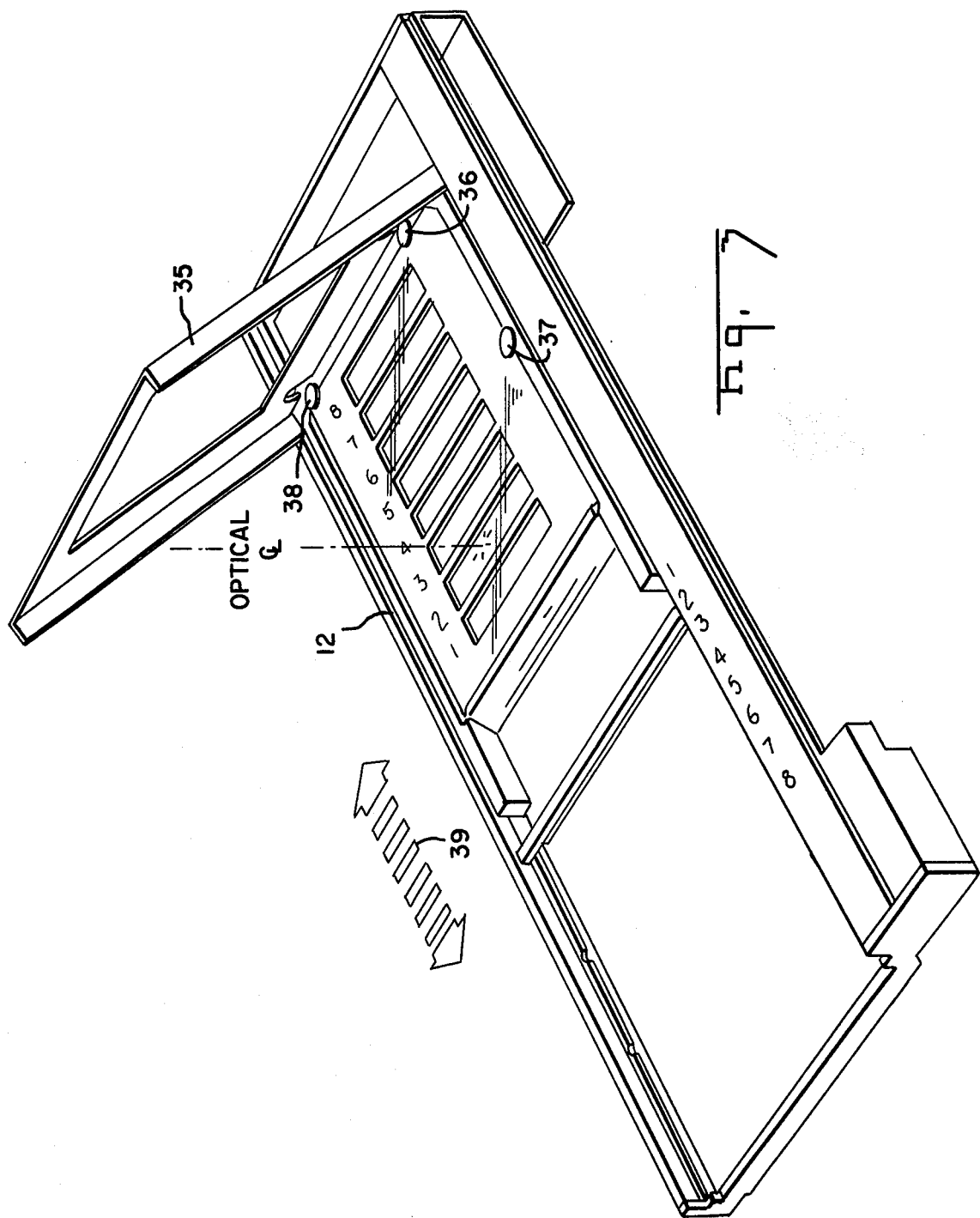
FIG. 3 shows the sample stage holder.

FIG. 3 shows the sample holder 12 which provides mechanical sample alignment. The sample has divisions between sample tracks and is completely dimensionally controlled for size and sample track locations. The sample is inserted under the hinged hold-down cover 35. Hold-down cover 35 holds the sample against three locating pins 36-38. This provides a three point reference which dimensionally locates the sample plate with respect to the sample holder 12 by two of its edges. This allows complete alignment, thereby obviating time-consuming visual alignment. This also eliminates alignment error and inaccurate results in quantification.

Sample holder 12 provides detented movement in the direction of the arrow 39. Detents engage notches in the tracks of the sample stage so the sample holder 12 can be indexed to any one of the eight track positions indicated by the numerals 1 through 8. With complete alignment assured for the sample tracks, it is possible to mechanically switch from track to track with the detenting movement on the stage.

Figure 4:
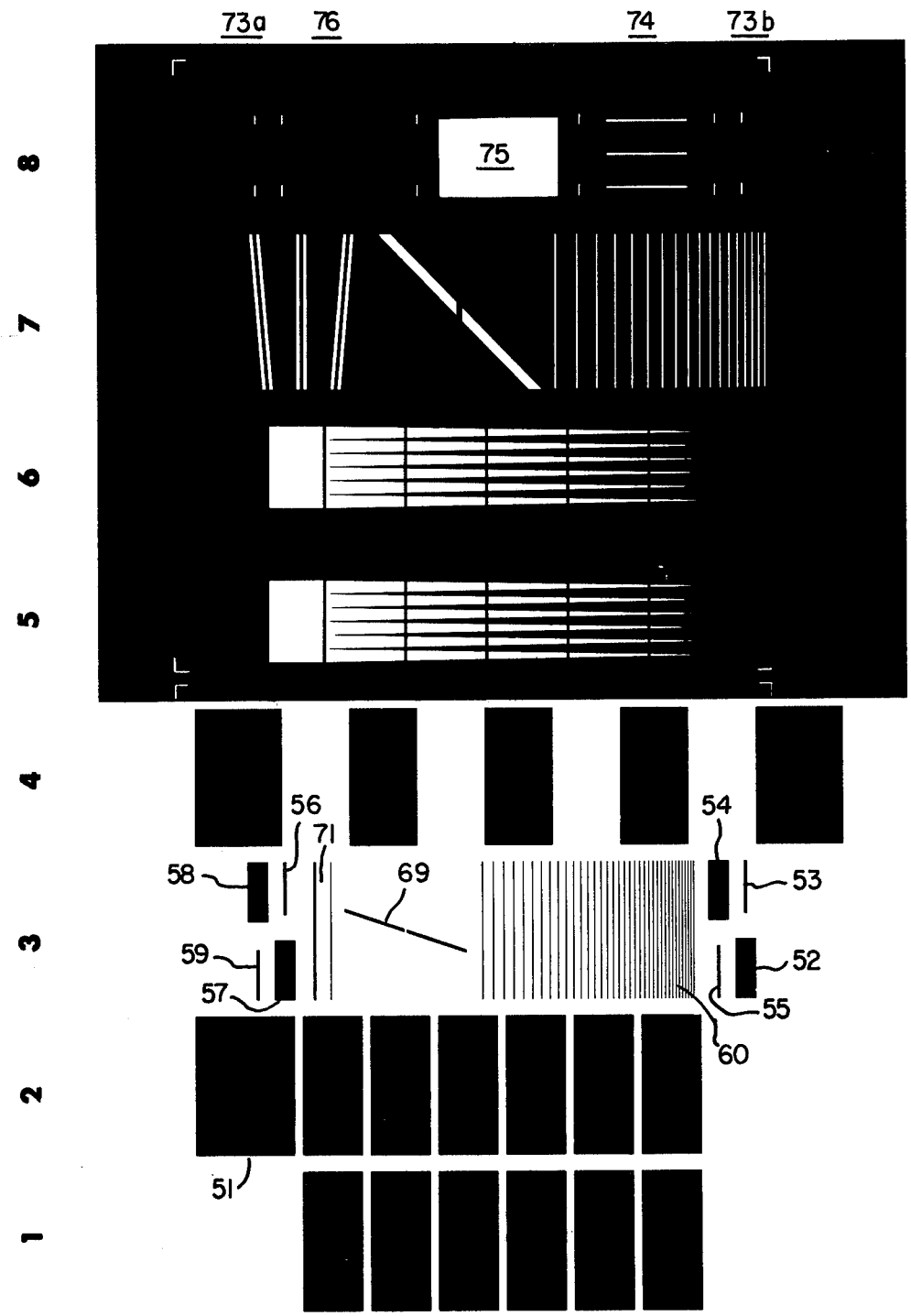
FIG. 4 shows a test sample provided in accordance with this invention.

A test sample for use in testing the instrument is shown in FIG. 4.

The sample shown in FIG. 4, has eight sample tracks. This test sample is produced by conrolled exposure and development of a commercial photographic film. Such film has inherent fluorescence when exposed to ultraviolet light. The exposed (black) areas of the film suppress this fluorescence. Alternatively, a phosphor film overlay can be used to generate fluorescent light with the black areas of the film samsple selectively blocking the light.

The test sample has eight tracks bearing geometric or optical density features which, when scanned, allow the operator to verify proper instrument function from the resulting analog and digital recorder outputs. In the description of FIG. 4 scanning of the tracks from left to right will be assumed. Tracks 1-4 are used for densitometry testing and tracks 4-8 are used for fluorometry testing. Analog outputs resulting from scanning the tracks of the test sample are shown in FIG. 5.

Track 1 includes six zones of different optical densities. Uniform increments in density with distance along the track allow densitometric nonlinearity to be determined as deviations in the output peak amplitudes from a straight line. Referring to FIG. 5 the analog output from track 1 shows six peaks of linearly increasing amplitude indicating that the response of the detector and its amplifiers to densitometric light is linear. The numbers above each of the peaks indicate the integrated area beneath each of the peaks as displayed on the digital indicator 19. The uniformly increasing area of the peaks indicates linearity.

Referring again to FIG. 4, there are low density intervals between the dense zones in track 1. This allows precise manual or automatic selection of the valleys which mark the separations between the peaks. As more fully described in copending application Ser. No. 800,005, filed May 24, 1977, the detected valleys are used to set the limits of integration for each of the peaks.

Track 2 includes zones of known optical density together with an opaque zone 51. The performance parameters associated with logarithmic processing of the signal can be determined by comparing the response 52 (FIG. 5) to the opaque zone with the response to zones of measurable density. The optical density corresponding to a zero light level (opaque zone) should be infinite, but the response of the logarithmic amplifier converting the transmitted light signal to a density signal will, in fact, be limited to a level correponding to some finite optical density. The densitometric response to the opaque peak is given by its output amplitude relative to the low density peaks. Departure of this response level from the expected value indicates electrical or optical offset at the logarithmic amplifier input, abnormal signal level or gain preceding the logarithmic amplifier or abnormal logarithmic amplifier saturation level.

Track 3 tests the alignment of the scanning path. Features 52-59 are offset from the center of the path of the densitometric or fluorometric slit. During an accurate scan equal portions of features 54, 52, 57 and 58 are intercepted. Displacement of the scan path in the direction of one of the features 52-59 generates a corresponding increase in output. The scanning slit is centered on the track as it passes zones 52 and 54 as evidenced by the equal heights of the peaks 61 and 62. However, the slit is displaced in the direction of zone 57 as evidenced by the fact that peak 63 is higher than peak 64.

Features of different shapes are used at different distances from the path center line to determine the amount of the displacement. In track 3 of FIG. 4, small lateral displacements cause the slit to intercept unequal portions of the wider blocks 52, 54, 57 or 58 whereas larger displacements cause interception of the finer lines 53, 55, 56 or 59. Because the features are bilaterally unsymmetric about the track center line, lateral and rotational misalignments can be distinguished. For example, if peaks 61 and 63 are greater than peaks 62 and 64, or vice versa, there is lateral misalignment. If peaks 61 and 64 are greater than peaks 62 and 63, or vice versa, there is rotational misalignment.

Track 3 also includes a series of fine lines 60 which are spatially arranged in geometric progression to determine slit resolution. When the detector is scanning a region with line spacing greater than the slit width, the detector usually senses only a single line and occasionally senses no lines. In this case the recorder output has spikes which extend downward from a signal level plateau corresponding to sensing of a single line. The spikes at 66 in FIG. 5 result from scanning the wider spaced lines. When the line spacing is somewhat less than the slit width, the slit contains at least one line and occasionally two lines. Spikes extending upward from the signal plateau are generated as evidenced by the zone 67 in the analog record of FIG. 5. The transition between the zones 66 the zone and 67 occurs at a point at which the line spacing is equal to the slit width. At this point, a spike free node 68 is observed in the analog output. The sharpness of the output transition is correlated with slit outline sharpness. The profile generated by the pulse amplitude extremes gives the instrument response to a fine line feature as a function of its displacement from the slit center line. Geometric spacing of the lines is not necessary but makes the spacing interval vary linearly with distance along the pattern, facilitating interpretation.

The same type of geometric line pattern is included in track 7 for testing slit resolution during operation in the fluorometric mode. Track 3 also contains a line 69 which is symmetrical but oblique to the slit and scan axes. In response to detection of this line the detector produces an output representing the lateral sensitivity profile of the slit. This output is shown at 70 in FIG. 5. The line 69 is broken in the middle to provide a distinct marker which permits assessment of the lateral slit alignment relative to the sample.

Track 7 contains a similar oblique line for testing the lateral sensitivity in the fluorometric mode.

Track 4 contains opaque or near opaque zones which are used to determine instrument noise and response time under extreme and rapid changes in signal level. These zones of identical density produce identical integrator outputs if the scan speed is uniform. Track 4 is also used for fluorometric testing. Uniform fluorometric response should result from scanning these equal zones.

Tracks 5 and 6 contain triangular, wedge shaped features which are used to generate a fluorescence signal that is linear with distance along the track. This tests the fluorometric linearity of the instrument. The straightness of the corresponding ramp in the analog record indicates a linear response to fluorometric light. The use of several small triangles, or wedges, provides a large signal while insuring that fluorometric light is uniform over the entire slit width. It is possible that fluorometric sensitivity might vary over the portion of the slit swept by a single large wedge and this would give rise to an erroneous indication of nonlinearity.

While triangular features have been shown in FIG. 4, triangles need not necessarily be used. The basic principle involved is the use of optically active zones having rectilinear, nonparallel boundaries to achieve a linear signal ramp.

Periodic interruptions in the wedges generate marks that allow precise manual or automatic valley selection. As a result, response linearity can be determined by comparing the integrated values for the pattern segments with nominal values determined from the pattern geometry. A phosphor-tape overlay is used to generate a higher fluorescence range for track 6. The fluorescence is sufficiently high to allow signal clipping to be observed and quantitated.

Track 7 contains, at the left-hand end, lines which are inclined with respect to the scan axis. These are used to determine rotational alignment of the optical slits. Rotational alignment of a slit with a feature results in maximized output. Several features with differently aligned axes are used to allow judgements to be made on the basis of relative rather than absolute signal magnitudes. The double bar structure of the features enhances the portion of the peak-amplitude signal coming from the edge area of the slit, thereby increasing the difference in signal for small differences in rotational alignment.

Track 8 contains sets of marks 73a and 73b which are spaced equidistant from the scan limits. These are used to test the longitudinal alignment of the sample relative to the scan limits. The fluorescence of feature 74 is smaller than that required to give a full-scale record at the maximum autogain setting of the instrument. The amplitude of peak 72 in FIG. 5, therefore, gives a proportional indication of the sensitivity of the instrument. Feature 74 also provides a reference signal level for other tests on this track. A hole 75 in the opaque background is used to determine the level of excitation or stray light energy entering the detector in the fluorometric mode.

The opaque zone 76 in track 8 allows determination of automatic zero accuracy at the maximum autogain level established by feature 74.

The test sample may be fabricated by camera imaging of a pattern negative onto a photographic emulsion on a plastic film back medium. Commercial photographic film is used. In general, however, any transparent, flat medium (such as glass or plastic plate) could be used as a backing medium, provided that it is thin enough to be inserted in the instrument to be tested. Optically dense features can be fabricated by controlled exposure to light of a photographic emulsion on the plate, as above, or by other processes such as thin-layer metal deposition or etching, etc. Required fluorescence of the pattern can be obtained by using the intrinsic fluorescence of the medium, by permanent or temporary painting, overlaying, or sandwiching of the medium with a material having fluorescence, or by doping of the medium with a fluorescent substance. For use in fluorometers with a "reflected light" geometry, the features could also be generated by application and/or removal of fluorescent material on an opaque support medium.

While a particular embodiment of the invention has been shown and described, various modifications are within the true spirit and scope of the invention. The appended claims are intended to cover all such modifications.

What is claimed is:

1. A method of testing an optical analyzer of the type which includes:

a source of analysis energy, and a sample stage movable linearly one with respect to the other to scan a sample across said source, a detector producing an output representing the optical characteristics in a track in said sample, and a recorder for recording the output of said detector, said method comprising:

scanning multiple tracks of a test sample which bear features that generate detector outputs indicating performance parameters of said analyzer, and recording said outputs as a record of said performance.

2. The method recited in claim 1 wherein the step of scanning includes scanning a test sample bearing features which generate a detector output indicating the linearity, range, resolution and alignment of said analyzer.

3. The method recited in claim 1 wherein said detector produces an output respresenting the densitometric characteristics of the light transmitted from said detector through said sample, said method further comprising testing the linearity of response of said detector by scanning zones of different optical densities on said test samples, said zones changing in uniform increments in density with distance along the track.

4. The method recited in claim 3 wherein one of said zones is opaque and wherein the recorded output of the detector in response to said opaque zone indicates the maximum response of said detector.

5. The method recited in claim 1 further comprising testing the alignment of said detector with respect to the scanning path by scanning features which are offset from the center line of a track to record an increase in said output corresponding with displacement of the scan path in the direction of said features.

6. The method recited in claim 5 wherein features of different shapes are positioned at different distances from said center line so that the response of said detector indicates the magnitude of the displacement of the analyzer scan path from the true center line scan path.

7. The method recited in claim 1 further comprising testing the resolution of the slit through which light from said sample impinges upon said detector, by scanning fine lines on said test pattern which are spatially arranged in geometric progression.

8. The method recited in claim 1 further comprising testing the lateral sensitivity of said detector by scanning a line on said test pattern which obliquely crosses the center line of the scan path.

9. The method recited in claim 1 further comprising testing the uniformity of the scan speed along a track by scanning zones of equal width and equal density on said test sample.

10. The method recited in claim 1 wherein said analysis energy is fluorescent light and wherein said detector produces an output representing the response of said sample to fluorometric light, said method further comprising testing the linearity of the output of said detector by scanning a feature which changes linearly in fluorescent response with distance along said scan path.

11. The method recited in claim 10 further comprising scanning parallel wedges having linearly changing area with scan distance and being laterally displaced across the width of the scan.

12. The method recited in claim 1 further comprising testing the fluorometric sensitivity of said detector by scanning a feature with a fluorescence smaller than that required to give a full scale output of said detector set at maximum sensitivity.

* * * * *